US006780614B2

(12) United States Patent
Négrier et al.

(10) Patent No.: US 6,780,614 B2
(45) Date of Patent: *Aug. 24, 2004

(54) MODIFIED FACTOR VIII CDNA AND ITS USE FOR THE PRODUCTION OF FACTOR VIII

(75) Inventors: Claude Négrier, Irigny (FR); Jean-Luc Plantier, Gringy (FR)

(73) Assignee: Aventis Behring GmbH, Marburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/067,894

(22) Filed: Feb. 8, 2002

(65) Prior Publication Data

US 2002/0182684 A1 Dec. 5, 2002

(30) Foreign Application Priority Data

Feb. 9, 2001 (EP) .............................. 01102810

(51) Int. Cl.⁷ ...................... C12N 15/00; C12N 15/63; C07H 21/04; C07K 1/00
(52) U.S. Cl. .................. 435/69.6; 435/69.1; 435/320.1; 435/425; 435/440; 514/44; 514/802; 514/834; 536/23.1; 536/23.5
(58) Field of Search ............................ 435/69.1, 320.1, 435/455, 69.6, 440, 425; 514/44, 802, 834; 536/23.1, 23.5

(56) References Cited

U.S. PATENT DOCUMENTS

| | | | |
|---|---|---|---|
| 5,112,950 A | 5/1992 | Meulien et al. | 530/383 |
| 6,271,025 B1 * | 8/2001 | Negrier et al. | 435/320.1 |
| 6,399,587 B1 | 6/2002 | Mehtali et al. | 514/44 |

FOREIGN PATENT DOCUMENTS

| | | |
|---|---|---|
| EP | 0 197 901 B1 | 10/1986 |
| EP | 0 295 597 A2 | 12/1988 |
| EP | 0 303 540 B1 | 2/1989 |
| EP | 1 038 959 A1 | 9/2000 |
| EP | 1 048 726 A2 | 11/2000 |
| EP | 1231220 A1 | 8/2002 |
| FR | 2 763 959 A | 12/1998 |
| WO | WO 87/04187 | 7/1987 |
| WO | WO 88/00831 | 2/1988 |
| WO | WO 92 16557 | 10/1992 |

OTHER PUBLICATIONS

Hao et al. Expression of Biologically Active Human Factor IX in Human Hematopoietic Cells after Retroviral Vector–Mediated Gene Transduction. (1995) Human Gene Therapy, vol. 6, pp. 873–880.*
U.K. Laemmli, "Cleavage of Structural Proteins during the Assembly of the Head of Bacteriophage T4," Nature, vik, 227, pp. 680–685 (1970).
Paul Martin, et al., "HEL Cells: A New Human Erythroleukemia Cell Line with Spontaneous and Induced Globin Expression," Science, vol. 216, pp. 1233–1235 (1982).

Jane Gitschier, et al., "Characterization of the human factor VIII gene," Nature, vol. 312, pp. 326–330 (1984).
Gordon A. Vehar, et al., "Structure of human factor VIII," Nature, vol. 312, pp. 337–342 (1984).
John J. Toole, et al., "Molecular cloning of a cDNA encoding human antihaemophilic factor," Nature, vol. 312, pp. 342–347 (1984).
A. Tabilio, et al., "Expression of platelet membrane glycoproteins and α–granule proteins by a human erythroleukemia cell line (HEL)," The EMBO Journal, vol. 3, No. 2, pp. 453–459 (1984).
L.–O. Andersson, et al., "Isolation and characterization of human factor VIII: Molecular forms in commercial factor VIII concentrate, cryoprecipitate, and plasma," *Proc. Natl. Acad. Sci. USA,* vol. 83, pp. 2979–2983, (1986).
Sheryl M. Greenberg, et al., "Characterization of a New Megakaryocytic Cell Line: The Dami Cell," *Blood,* vol. 72, No. 6, pp. 1968–1977 (1988).
Michael W. Long, et al., "Regulation of Megakaryocyte Phenotype in Human Erythroleukemia Cells," The American Society for Clinical Investigation, Inc. , vol. 85, pp. 1072–1084 (1990).
Georges Uzan, et al., "Tissue–specific Expression of the Platelet GPIIb Gene," The Journal of Biological Chemistry, vol. 266, No. 14, Issue of May 15, pp. 8932–8939 (1991).
Catherine P. M. Hayward, et al., "Multimerin Is Found in the α–Granules of Resting Platelets and Is Synthesized by a Megakaryocytic Cell Line," The American Society for Clinical Investigation, Inc., vol. 91, pp. 2630–2639 (1993).
Karen K. Ballen, et al., "Expression and activation of protein kinase C isoforms in a human megakaryocytic cell line," Experimental Hematology, pp. 24: 1501–1508 (1996).
Stephen A. Hill, et al., Differential Mechanisms Targeting Type 1 Plasminogen Activator Inhibitor and Vitronectin Into the Storage Granules of a Human Megakaryocytic Cell Line, *Blood,* vol. 87, No. 12, pp. 5061–5073 (1996).
Hans Van Der Vuurst, et al., "Maturation of Megakaryoblastic Cells Is Accompanied by Upregulation of $G_s\alpha$–L Subtype and Increased camp Accumulation," Thromb Haemost, 79: 1014–1020 (1998).
Baatout, S et al., "Protein content and number of nucleolar organizer regions are enhanced during phorbol ester–induced differentiation of cultured human megakaryocytic cells," *Anticancer Research,* 19:3229–3235 (1999).
Hill, S. et al., "Differential mechanisms targeting type 1 plasminogen activator inhibitor and vitronectin into the storage granules of a human megakaryocytic cell line," *Blood,* 87(12):5061–5073 (1996).

(List continued on next page.)

*Primary Examiner*—Christopher S. F. Low
*Assistant Examiner*—Holly Schnizer
(74) *Attorney, Agent, or Firm*—Finnegan, Henderson, Farabow, Garrett and Dunner, L.L.P.

(57) ABSTRACT

A modified Factor VIII cDNA is disclosed wherein the B-domain of the wild type factor cDNA has been deleted and a truncated Factor IX intron 1 has been inserted in two locations of the Factor VIII cDNA and as a promoter a cDNA is used which is suitable for the expression in hematopoietic cell lines and specifically in platelets.

10 Claims, 4 Drawing Sheets

OTHER PUBLICATIONS

Hoeben, R.C. et al., "Toward gene therapy in haemophilia: A retrovirus–mediated transfer of a factor VIII gene into murine haematopoietic progenitor cells," *Thrombosis and Haemostasis*, 67(3):341–345 (1992).

Plantier, J.–L. et al., "A combination of truncated factor IX intron I highly improves FVIII production," *Blood*, 94(10) Suppl. 1 Part 1:454a (1999).

Plantier, J.–L. et al., "A factor VIII minigene comprising the truncated intron I of factor IX highly improves the in vitro production of factor VIII," *Thrombosis and Haemostasis*, 86(2):596–603 (2001).

Uzan, G. et al., "Tissue–specific expression of the platelet GPIIB gene," *Journal of Biological Chemistry*, 266(14):8932–8939.

Derwent abstract of EP 0 295 597 A2.

Derwent abstract of EP 0 303 540 B1.

Brinkhous et al., "Purified human factor VIII procoagulant protein: Comparative hemostatic response after infusions into hemophilic and von Willebrand disease dogs," *Proc. Natl. Acad. Sci. USA*, 82:8752–8756 (1985).

Buchman et al., "Comparison of Intron–Dependent and Intron–Independent Gene Expression," *Molecular and Cellular Biology*, 8(10):4395–4405 (1988).

Burke et al., "The Functional Domains of Coagulation Factor VIII:C*," *The Journal of Biological Chemistry*, 261(27):12574–12578 (1986).

Connelly et al., "High–Level Tissue–Specific Expression of Functional Human Factor VIII in Mice", *Human Gene Therapy*, 7(2):183–195 (1996).

Andrew J. Dorner et al., "The Relationshhip of N–linked Glycosylation and Heavy Chain–Binding Protein Association with the Secretion of Glycoproteins," *The Journal of Cell Biology*, 105(6):2665–2674 (1987).

Eaton et al., "Construction and Characterization of an Active Factor VIII Variant Lacking the Central One–Third of the Molecule," *American Chemical Society*, 25(26):8343–8347 (1986).

Fallaux et al., "The Human Clotting Factor VIII cDNA Contains an Autonomously Relicating Sequence Consensus– and Matrix Attachment Region–Like Sequence That Binds a Nuclear Factor, Represses Heterologous Gene Expression, and Mediates the Transcriptional Effects of Sodium Butyrate," *Molecular and Cellular Biology*, 16(8):4264–4272 (1996).

Foster et al., "Factor VIII Structure and Function," *Blood Reviews*, 3:180–191 (1989).

Kaufman, "Biological Regulation of Factor VIII Activity," *Annu. Rev. Med.* 43:325–39 (1992).

Kaufman et al., "Effect of von Willebrand Factor Coexpression on the Synthesis and Secretion of Factor VIII in Chinese Hamster Ovary Cells," *Molecular and Cellular Biology*, 9(3):1233–1242 (1989).

Kim et al., "Heterologous Introns Enhanced Expression of Human Lactoferrin cDNA in Mouse Mammary Epithelial Cells," *J. Biochem. Mol. Biol.*, 28(1):57–61 (1995).

Dwight D. Koeberl et al., "Sequences Within the Coding Regions of Clotting Factor VIII and CFTR Block Transcriptional Elongation," *Human Gene Therapy*, 6:469–479 (1995).

Kurachi, "Role of Intron I in Expression of the Human Factor IX Gene," *The Journal of Biological Chemistry*, 270(10):5276–5281 (1995).

Langner et al., "Synthesis of Biologically Active Deletion Mutants of Human Factor VIII:C," *Behring Inst. Mitt.*, 82:16–25 (1988).

Lind et al., "Novel forms of B–domain–deleted recombinant factor VIII molecules Construction and biochemical characterization," *Eur. J. Biochem.* 232:19–27 (1995).

Lynch et al., "Sequences in the Coding Region of Clotting Factor VIII Act as Dominant Inhibitors of RNA Accumulation and Protein Production," *Human Gene Therapy*, 4:259–272 (1993).

Meulien et al., "A new recombinant procoagulant protein derived from the cDNA encoding human factor VIII," *Protein Engineering*, 2(4):301–306 (1988).

Nichols et al., "Mutations in the ER–Golgi Intermediate Compartment Protein ERGIC–53 Cause Combined Deficiency of Coagulation Factors V and VIII," *Cell*, 93:61–70 (1998).

Paviranii et al ., Two Independent Domains of Factor VIII Co–Expressed Using Recombinant Vaccinia Viruses Have Procoagulant Activity, *Biochem. Biophys. Res. Comm.*, 145 (1):234–240 (1987).

Pipe et al., "Differential Interaction of Coagulation Factor VIII and Factor V with Protein Chaperones and Calnexin and Calreticulin," *Journal of Biological Chemistry*, 273(14):8537–8544 (1998).

Pittman et al., "Role of the B Domain for Factor VIII and Factor V Expression and Function," *Blood*, 84(12):4214–4225 (1994).

Pittman et al., "Biochemical, Immunological, and In Vivo Functional Characterization of B–Domain–Deleted Factor VIII," *Blood*, 81(11):2925–2935 (1993).

Sarver et al., "Stable Expression of Recombinant Factor VIII Molecules Using a Bovine Papillomavirus Vector," *DNA*, 6(6):553–564 (1987).

Wood et al., "Expression of active human factor VIII from recombinant DNA clones," *Nature*, 312:330–337 (1984).

Vlot et al., "Factor VIII and von Willebrand Factor," *Thromb Haemost* 79:456–65 (1998).

Hoeben et al., "Expression of the Blood–Clotting Factor VIII cDNA Is Repressed by a Transcriptional Silencer Located in Its Coding Region," *Blood*, 85:2447–2454 (1995).

Toole et al., "A Large Region (≈95 kDa) of Human Factor VIII is Dispensable for in vitro Procoagulant Activity," *Proc. Natl. Acad. Sci. USA*, 83:5939–5942 (1986).

* cited by examiner

MODIFIED FACTOR VIII CDNA AND ITS USE FOR THE PRODUCTION OF FACTOR VIII

This invention is directed to a modified Factor VIII cDNA and its use for the improvement of the Factor VIII production.

Factor VIII (FVIII) is a X-linked gene product implicated in the blood coagulation cascade. The factor VIII is synthetized as a 2351 amino acid single-chain polypeptide having the domain structure A1-A2-B-A3-C1-C2 and comprising a 19 amino acid signal peptide (Gitschier J. et al., 1984; Toole, J. J. et al., 1984; Vehar, G. A. et al., 1984). Plasma FVIII is a heterodimer consisting of a carboxy-terminal derived light chain of 80 kDa in a metal-ion dependent association with a variable sized amino-terminal heavy chain (200–90 kDa; Andersson et al., 1986). Absence or deficiency of FVIII causes severe bleeding disorders called hemophilia A.

The level of FVIII production remains low after cell transfection compared to other genes. Three reasons have been identified so far: (1) FVIII mRNA is inefficiently produced, (2) FVIII translocation from endoplasmic reticulum to Golgi apparatus is low and (3) FVIII is sensitive to proteolysis. Therefore, the improvement of FVIII transgenes is an important challenge for hemophilia A gene therapy.

It has already been proposed in the European patent application 99 104 050.2 to modify the FVIII cDNA by deleting the B-domain of the wild type cDNA and by inserting a truncated FIX intron 1 in different locations of the Factor VIII cDNA. Such modified Factor VIII cDNA may be used for a higher yield production of FVIII in vitro as well as in a transformation vector for gene therapy. A cDNA bearing the FIX truncated intron 1 in both the intron 1 and intron 13 locations led to the highest FVIII production after transfection of CHO and HepG2 cell lines. This recombinant FVIII was a biologically active protein.

In order to further improve the yield in the gentechnological production of Factor VIII the present invention is directed to the expression of Factor VIII in hematopoietic cells and especially in platelets using the tissue-specific promoter of the glycoprotein II b (GPIIb).

The feasitility of this approach was demonstrated, first by use of the hematopoietic cell line HEL. The human erythroleukemia cell line is known to express an erythroid phenotype (Martin et al., 1982) but also some megakaryocytic markers such as platelet membrane glycoproteins (Tabilio et al., 1984). Upon induction by phorbol-12-myristate-13-acetate (PMA), HEL cell line expresses increased amounts of megakaryocytic proteins like glycoproteins IIb/IIIa, Platelet factor 4, or von Willebrand factor (vWF) (Long and coll., 1990).

Another hematopoietic cell line, Dami, established from the blood of a patient with a megakaryoblastic leukaemia, appears to be a pure population of megakaryocyte-like cells (Greenberg et al., 1988). Cultured Dami cells express platelet glycoproteins GPIIb and GPIIb/IIIa. After PMA stimulation, surface expression of these two platelet glycoproteins, and vWF synthesis were increased. These changes were associated with a decrease in the proliferation of the stimulated Dami cells (Greenberg et al., 1988; Ballen et al., 1996; von der Vuurst et al., 1998). The multimerin molecule, which colocalizes with vWF in platelet α-granules, was shown to be synthetized in PMA-stimulated Dami cells where it presented a granular distribution (Hayward et al., 1993). The same results were obtained with the plasminogen activator inhibitor type I and vWF (Hill et al., 1996). Dami cells were used to study the megakaryocyte-specific expression of FVIII under the GPIIb promoter control.

The present invention discloses the ability of hematopoietic cell lines to produce an active FVIII molecule. It could be demonstrated that Dami cells transfected with the GPIIb constructs are able to synthetize FVIII and that FIX intron 1 sequences increase dramatically the production of Factor VIII.

A modified Factor VIII cDNA has been found wherein the B-domain of the wild type factor cDNA has been deleted and a truncated Factor IX intron has been inserted in two locations of the Factor VIII cDNA containing as a promoter a cDNA which is suitable for the expression in hematopoietic cell lines and specifically in platelets. The cDNA coding for the human platelet glycoprotein IIb (GPIIb) is preferred as a promoter. The modified Factor VIII cDNA of the present invention contains the truncated Factor IX intron 1 in the Factor VIII introns 1 and 13.

A further object of the invention is a process for the production of Factor VIII in the cell lines HEL or Dami using the above-mentioned modified Factor VIII cDNA. Preferred is a process wherein the production of Factor VIII is stimulated by an inducer. The best results have been obtained when phorbol-12-myristate-13-acetate (PMA) was used.

Materials and Methods

Vectors: The pcDNA3-FVIII and pcDNA3-FVIII I1+13 were the same vectors as disclosed in the European patent application 99 104 050.2. The pBLCAT3-vector bearing the −643/+33 GPIIb promoter was obtained from G. Uzan (Uzan et al., 1991). This promoter was sorted from the pBLCAT3-GPIIb vector after HindIII-BamHI digestion (Promega, Charbonnières, France) and was introduced in pcDNA3.1 vector (Invitrogen, Groningen, The Netherlands) opened by the same enzymes. This construct was then deleted of the CMV promoter by MluIClaI digestion, and the construct obtained was so called pcDNA3-GPIIb. The pTracer™-EF C vector was obtained from Invitrogen (Groningen, The Netherlands). This vector is bearing a Zeozine™ resistance gene.

Cell Culture: HEL92.1.7 was obtained from ECACC (Sophia Antipolis, France). The cells were maintained in RPMI/10% FCS medium with 5% $CO_2$. For stable transfections with pcDNA3 constructs, HEL cells ($1 \times 10^6$ cells) were transfected with 2 μg of PvuI linearized plasmid using 6 μl FUGENE™ 6 (Roche Diagnostics, Meylan, France) during 5 hours. After incubation, the cells were harvested and placed in fresh medium supplemented with 0,6 mg/ml geneticin (Gibco BRL, Cergy Pontoise, France).

Dami cells were maintained in RPMI/10% FCS medium with 5% C02. For stable transfections with pTracer constructs, Dami cell ($1 \times 10^6$ cells) were transfected with 2 μg of PvuI linearized plasmid using 6 μl FUGENE™ during 5 hours. The cells were then harvested and placed in fresh medium. Zeocin™ (Invitrogen, Groningen, The Netherlands) was subsequently added at a final concentration of 300 μg/ml.

Cell Inductions: To compare FVIII production, the resistant cells ($2.5 \times 10^5$ cells/ml) were placed in RPMI/1% BSA with human vWF ±PMA 1 nM. After 4 days of incubation, the cells were numbered and the supernatants were harvested. The supernatants were concentrated on Microsep™ microconcentrators (Pall Gelman Sciences, France) with a 30 Kd cut-off. The cells were lysated in Hepes 20 mM, KCl 0.1 M, $MgCl_2$ 2 mM, Tritonx100 0.5%. Protein concentrations were measured using Bio-Rad $D_c$ Protein Assay (Bio-Rad, Ivry sur Seine, France). FVIII productions were measured using FVIII ELISA kit (Asserachrom FVIII, Stago Asnières, France). Concentrated culture media were tested for coagulation activity using a chromogenic FVIII assay (Coamatic FVIII, Biogenic, France).

RT-PCR and PCR: Reverse transcriptase (RT) reactions were realized with 2 μg mRNA (extracted with Rneasy Mini kit; QIAGEN S. A., France) using the Superscript™ Rnase H Reverse transcriptase (Gibco BRL, Cergy Pontoise, France) and oligo(dT)$^{15}$ primer (Promega, Charbonnières, France). For PCR, Expand™ long template PCR system (Roche Diagnostics, Meylan, France) was used with 4 μl of each RT product or 10 ng of each control plasmid. Intron splicing was studied using a set of primers specific for intron 1 location and another set for intron 13 location. The first PCR gives a 1701 bp fragment without the intronic sequence and a 2014 bp fragment with the FIX intron 1 sequence. With the 2 other primers, the size of PCR fragments was 623 bp and 935 bp depending upon the absence or the presence of intron 13, respectively. RT-PCR and PCR fragments were run on 0.8% agarose gel and were compared with the 1 Kb ladder (Gibco BRL, Cergy Pontoise, France).

Immunoprecipitations and FVIII Immunoblot Analysis: Before immunoprecipitations, lysates were incubated with human vWF (2,000 ng vWF for 40 ng FVIII; Diagnostica Stago, Asnières, France) for 10 min at room temperature. Fifty microliters of anti human vWF antibody beads provided by Aventis Behring (USA) were added to the samples and incubated overnight at 4° C. The beads were then collected after centrifugation (2 min at 2500 rpm), washed three times with the equilibration buffer (Hepes 10 mM, KCl 100 mM, MgCl$_2$ 2 mM, Tritonx100 0.1%) and diluted in Laemmli buffer (Laemmli, 1970). Samples were then subjected to electrophoresis on SDS-PAGE/7% polyacrylamide gel and semi-dry blotted onto Hybond™ C Pure membrane (Amersham Pharmacia Biotech Europe GmbH, France) The immunoblots were blocked with TBS-T (Tris-HCl 10 mM pH 7.5, NaCl 0.15 M, Tween 0.1%) for 1 h at room temperature and then incubated with 1:3,000 dilution of a sheep anti-human FVIII antibody (Cedarlane, Ontario, Canada). The membrane was then washed 3 times in TBS-T and incubated with a 1:10.000 dilution of a peroxydase-labeled anti-sheep antibody (Dako S. A., Trappes, France) for 30 min. After 3 washes, chemiluminescent signal was detected by autoradiography using the ECL System (Amersham Pharmacia Biotech Europe GmbH, France).

The following results were obtained:

1. FVIII Expression under CMV Promoter Control 1.1 FVIII Production in HEL Cells In order to compare FVIII productions with the same CMV promoter, HEL cells were stably transfected with pcDNA3-FVIII and pcDNA3-FVIII I1+13. pcDNA3.1 vector was used as negative control (Invitrogen, Groningen, The Netherlands). G418-resistant cells were thereafter compared.

No FVIII was detected in the supernatants of lysates of the pcDNA3.1 control cells. Without PMA stimulation, FVIII was detectable neither in the supernatants nor in the lysates of HEL cells. When 1 nM PMA was added to the cell culture, FVIII was detected in the CMV-FVIII- and CMV-FVIII I1+13-expressing cells (Table 1). In the supernatants, FVIII production was 13-fold higher with the CMV-FVIII I1+13 transfected cells compared to the CMV-FVIII-expressing cells. The intracellular FVIII amount was also higher in the CMV-FVIII I1+13 cells (2,5-fold increase).

TABLE 1

FVIII production by PMA-stimulated HEL cells.
$5 \times 10^5$ G418-resistant HEL cells were placed in 2 ml RPMI/1% BSA/1 nM PMA for 4 days. The supernatants were thereafter harvested and the cells were suspended in 250 μl of lysis buffer. FVIII was quantified using FVIII ELISA kit. Results are expressed as the mean values ± SEM of 4 individual experiments. pcDNA3 was used as reference for statistics (** represents p < 0.01).

|  | pcDNA3 | CMV-FVIII | CMV-FVIII I1 + 13 |
|---|---|---|---|
| Supernatants (ng/ml) | 0 ± 0 | 0,22 ± 0,05 | 2,97 ± 0,26 ** |
| Lysates (ng/mg of proteins) | 0 ± 0 | 1,38 ± 0,22 | 3,77 ± 0,26 ** |

1.2 FVIII Coagulant Activity

CMV-FVIII 1+13 HEL cells were placed in induction conditions with 1 nM PMA. After 4 days, the conditioned media were harvested, concentrated and FVIII antigen and FVIII coagulant activity were then quantified. The results demonstrated that HEL-produced FVIII was an active molecule (Table 2). The mean specific activity was 4.858.9±798.8 U/mg that was very similar to the specific activity of plasma FVIII.

TABLE 2

FVIII coagulant activity in the supernatants of PMA stimulated CMV-FVIII I1 + 13 HEL cells. CMV-FVIII I1 + 13 HEL cells were placed in the induction conditions for 4 days. FVIII antigen and FVIII coagulant activity were then quantified in the concentrated supernatants. Two independent experiments were presented. The results are expessed as the mean values ± SEM (n = 3)

|  | FVIII Antigen (ng/ml) | Coagulation activity (mU/mL) | Specific activity (U/mg) |
|---|---|---|---|
| Exp. 1 | 6,24 ± 0,70 | 33,58 ± 8,15 | 5.335.0 ± 882,7 |
| Exp. 2 | 12,04 ± 0,62 | 52,85 ± 6,64 | 4.382,9 ± 369,2 |
|  |  |  | 4.858,9 ± 798,8 |

1.3 Splicing of FIX Intron 1

Transfected HEL cells were incubated in RPMI-1% BSA-1 nM PMA medium during 3 days. RNAs were extracted and used for RT-PCR reactions. In pcDNA3-transfected HEL cells, no fragment was obtained with the 2 sets of primers. The 1701 and 623 bp fragments were essentially detected in the RT-PCR realized with mRNA from CMV-FVIII I1+13 transfected HEL cells demonstrating that the intronic sequences were correctly spliced. Conversely, the control plasmid pcDNA3-FVIII I1+13 exhibited the 2014 bp and 935 bp fragments, corresponding to the detection of introns 1 and 13.

1.4 FVIII Immunoblot Analysis

To further analyse FVIII recombinant proteins in HEL supernatants. FVIII was purified using beads coupled with an anti-human vWF antibody (provided by Aventis Behring). PcDNA3 and pcDNA3-FVIII I1+13 transfected HEL cells were incubated in RPMI-1% BSA-1 nM PMA medium supplemented with hu vWF (150 ng/mL). Supernatants were then concentrated on Microsep™ microconcentrators with a 30 Kd cut-off. The immunoprecipited proteins were then subjected to electrophoresis and FVIII immunoblot analysis. ReFacto®, a therapeutic recombinant B-domain deleted FVIII (Wyeth Genetics Institute) was used as control FVIII. The result is presented in FIG. 1. The immunoblot analysis detected both the FVIII light and heavy chains and demonstrated that the recombinant FVIII produced by CMV-FVIII I1+13 HEL cells presented the same protein profile as ReFacto®.

2. FVIII Expression under GPIIb Promoter Control 2.1 Obtention of pTracer-GPIIb Constructs The lineage-specific promoter GPIIb was chosen to express FVIII transgenes in the hematopoietic cell line Dami. The pBLCAT vector bearing the −643/+33 GPIIb promoter was obtained from G. Uzan (Uzan, 1991 #44). This promoter was sorted from the pBLCAT-GPIIb vector after HindIII-BamHI digestion (Promega, Charbonnières, France). It was introduced in pcDNA3.1 vector (Invitrogen, Leek, The Netherlands) opened by the same enzymes. This construct was then deleted of the CMV promoter by MluI-ClaI digestion, and was so called pcDNA3-GPIIb. This GPIIb vector bearing the −597/+33 GPIIb promoter is already disclosed in the European patent application 99 107 397.4.

PTracer™-EF C was opened by NruI-SpeI digestion. This enzyme digestion deleted the EF-1α promoter from the initial vector. The same digestion was used to extract the GPIIb promoter from pcDNA3-GPIIb plasmid. The 2 fragments were then ligated and the resulting expression plasmid was called pTracer/GPIIb.

In order to obtain pTracer/GPIIb-FVIII, pTracer/GPIIb was digested by NotI and BclI (FIG. 3). This digestion eliminated V5 epitope and the polyhistidine region of the initial pTracer-EF C vector (FIG. 2). pcDNA3-FVIII was treated by NotI, BclI and PvuI. The 2 resulting FVIII fragments (446 bp and 3973 bp) were extracted from agarose gel, and pTracer/GPIIb-FVIII was obtained with a triple ligation. The same strategy was used for pTracer/GPIIb-FVIII I1+13.

2.2 FVIII Production in Dami Cells

Dami cells were stably transfected using Zeocin selection. PTracer/GPIIb was used as negative vector control. Three pools were obtained for each GPIIb constructs. The cells were placed in induction conditions and FVIII was quantified in both the supernatants and the cell lysates.

In all the lysates no FVIII was produced in Dami cells transfected with pTracer/GPIIb. Conversely, FVIII was detected in the lysates of GPIIb-FVIII and GPIIb-FVIII I1+13 Dami cells (Table 3). Without PMA stimulation, GPIIb-FVIII I1+13-expressing cells produced about 25-fold higher FVIII than GPIIb-FVIII-expressing Dami cells. When the cells were incubated with PMA, the FVIII production was increased (6-fold increase for GPIIb-FVIII-transfected cells and 4-fold increase with the GPIIb-FVIII I1+13-expressing cells). The difference in FVIII production between FVIII and FVIII I1+13-transfected Dami cells was statistically significant ($p<0.05$ without PMA and $p<0.01$ with PMA).

In the supernatants, no FVIII was detected with Dami cells transfected with pTracer/GPIIb. Without PMA, the GPIIb-FVIII I1+13-expressing cells produced about 7.5-fold higher FVIII than the GPIIb-FVIII-expressing cells. A significant increase in FVIII production was measured in the supernatants following PMA stimulation. However, GPIIb-FVIII I1+13-expressing cells produced always more FVIII than the GPIIb-FVIII Dami cells.

These results demonstrated that Dami cells transfected with GPIIb-FVIII I1+13 produced significantly more FVIII than the GPIIb-FVIII-expressing cells.

TABLE 3

FVIII production(ng FVIII/mg of proteins in Dami cell lysates. $5 \times 10^5$ Zeocin-resistant Dami cells were placed in 2 ml RPMI/1% BSA ± 1 nM PMA for 4 days. The supernatants were thereafter harvested and the cells were suspended in 250 μl of lysis buffer. FVIII was quantified using FVIII ELISA kit. Results are expressed as the mean values ± SEM of 3 individual experiments. pTracer/GPIIb was used as reference for statistics (** represents $p < 0,01$).

|  | PTracer/GPIIb | GPIIb-FVIII | GPIIb-FVIII I1 + 13 |
|---|---|---|---|
| Without PMA | 0 ± 0 | 0,62 ± 0,37 | 15,81 ± 11,06 ** |
| With 1 nM PMA | 0 ± 0 | 3,66 ± 2,19 | 62,92 ± 28,27 ** |

2.3 FVIII Coagulant Activity

The FVIII coagulant activity was measured in concentrated supernatants using a chromogenic test. The results are presented in Table 4. No coagulant activity was detected in the supernatants from Dami cells transfected with GPIIb (data not shown). Conversely, a FVIII coagulant activity was found in the supernatants of GPIIb-FVIII I1+13-expressing Dami cells, and the specific activity was calculated to be 4.622.3+1.061.4 U/mg. The correlation between FVIII antigen and FVIII coagulant acitivity demonstrated that recombinant FVIII produced in Dami cells was a biologically active FVIII.

TABLE 4

FVIII coagulant activity in supernatants of PMA-stimulated GPIIb-FVIII I1 + 13 Dami cells. GPIIb-FVIII I1 + 13 Dami cells were placed in the induction conditions for 4 days. FVIII antigen and FVIII coagulant activity were then quantified in the concentrated supernatants. The results are expresed as the mean values ± SEM (n = 5).

|  | FVIII Antigen (ng/ml) | Coagulation activity (mU/ml) | Specific activity (U/mg) |
|---|---|---|---|
| Concentrated supernatants | 29,96 ± 5,28 | 142,53 ± 53,12 | 4.622,3 ± 1.061,4 |

2.4 FIX Intron 1 Splicing

In order to verify the correct splicing of the 2 FIX intron 1 sequences, RT-PCR analysis was realized. mRNAs were extracted from the unstimulated or PMA-stimulated transfected cells after 3 days of induction (Rneasy Mini Kit; Qiagen, Courtaboeuf, France). A PCR using pTracer/GPIIb-FVIII and pTracer/GPIIb-FVIII I1+13 were used as controls. RT-PCR results demonstrated that the FVIII mRNA was essentially spliced in GPIIb-FVIII I1+13 Dami cells. Dami cells were therefore able to correctly process FVIII mRNAs.

2.5 FVIII Immunoblot Analysis

To further analyse FVIII protein profile, beads coupled with an anti-human vWF monoclonal antibody were used (provided by Aventis Behring). Cell inductions were realized with human vWF (400 ng/ml) in the induction medium. The supernatants were concentrated and immunoprecipitated with the beads bearing an anti-human vWF monoclonal antibody. For the cell lysates, human vWF was added to the samples just before immunoprecipitations with the anti-human vWF antibody (Without adding human vWF after cell lysis, we were unable to immunoprecipitate FVIII). In pTracer/GPIIb Dami cells lysates or supernatants, no FVIII was detected (FIG. 4).

The recombinant FVIII produced by the GPIIb-FVIII I1+13-transfected Dami cells presented a protein profile very similar to the therapeutic recombinant B-domain-deleted FVIII (ReFacto®, Wyeth Genetics Institute).

The results of the present invention were obtained with 2 cell lines, HEL and Dami. These hematopoietic cell lines are able to produce a biologically active recombinant FVIII. This in vitro-produced FVIII presents a correct protein profile, essentially similar to a therapeutic B domain-deleted recombinant FVIII (ReFacto®, Wyeth Genetics Institute). The presence of 2 factor IX truncated introns in the FVIII I1+13 construct is responsible for a dramatic increase in FVIII production, and confirmed an ubiquitous effect of these FIX intron 1 sequences. The results obtained with GPIIb constructs-transfected Dami cells demonstrated that GPIIb promoter is able to efficiently improve the tissue-specific production of recombinant B domain-deleted FVIII in Dami cells. These results confirm that the GPIIb promoter controls the specific production of coagulation factor in hematopoietic cells and specifically in megakaryocytic oriented cells.

REFERENCES

Figure 1:
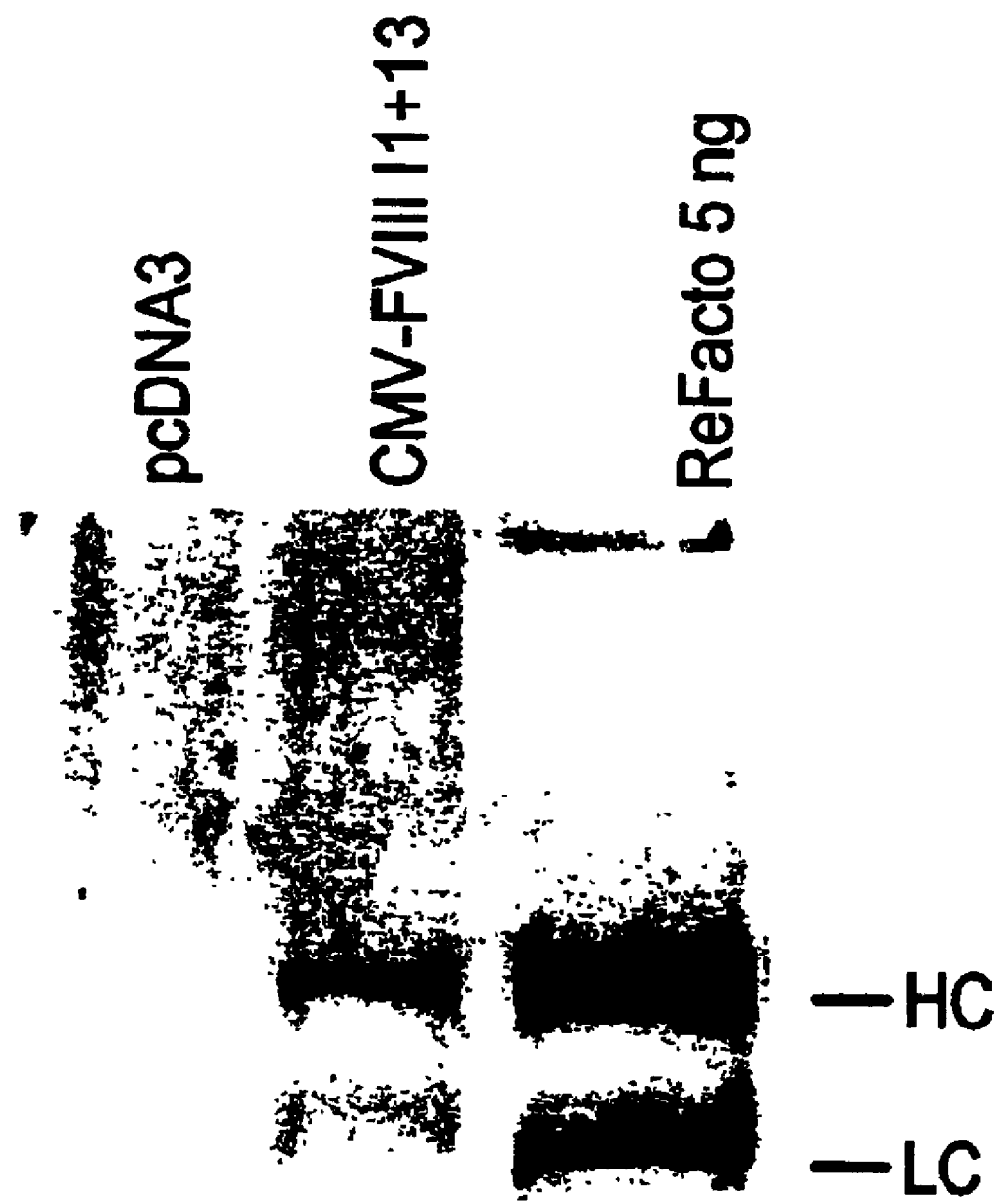
FIG. 1: Immunoblot Analysis of the Immunoprecipited FVIII Produced by the Transfected HEL Cells. PcDNA3- and CMV-FVIII I1+13 HEL cells were incubated with human vWF and PMA for 4 days. Supernatants were concentrated and thereafter subjected to vWF immunoprecipitation. FVIII immunoblot analysis was realized using an anti-human FVIII antibody and detected the light chain (LC) and the heavy chain (HC).
Figure 2:
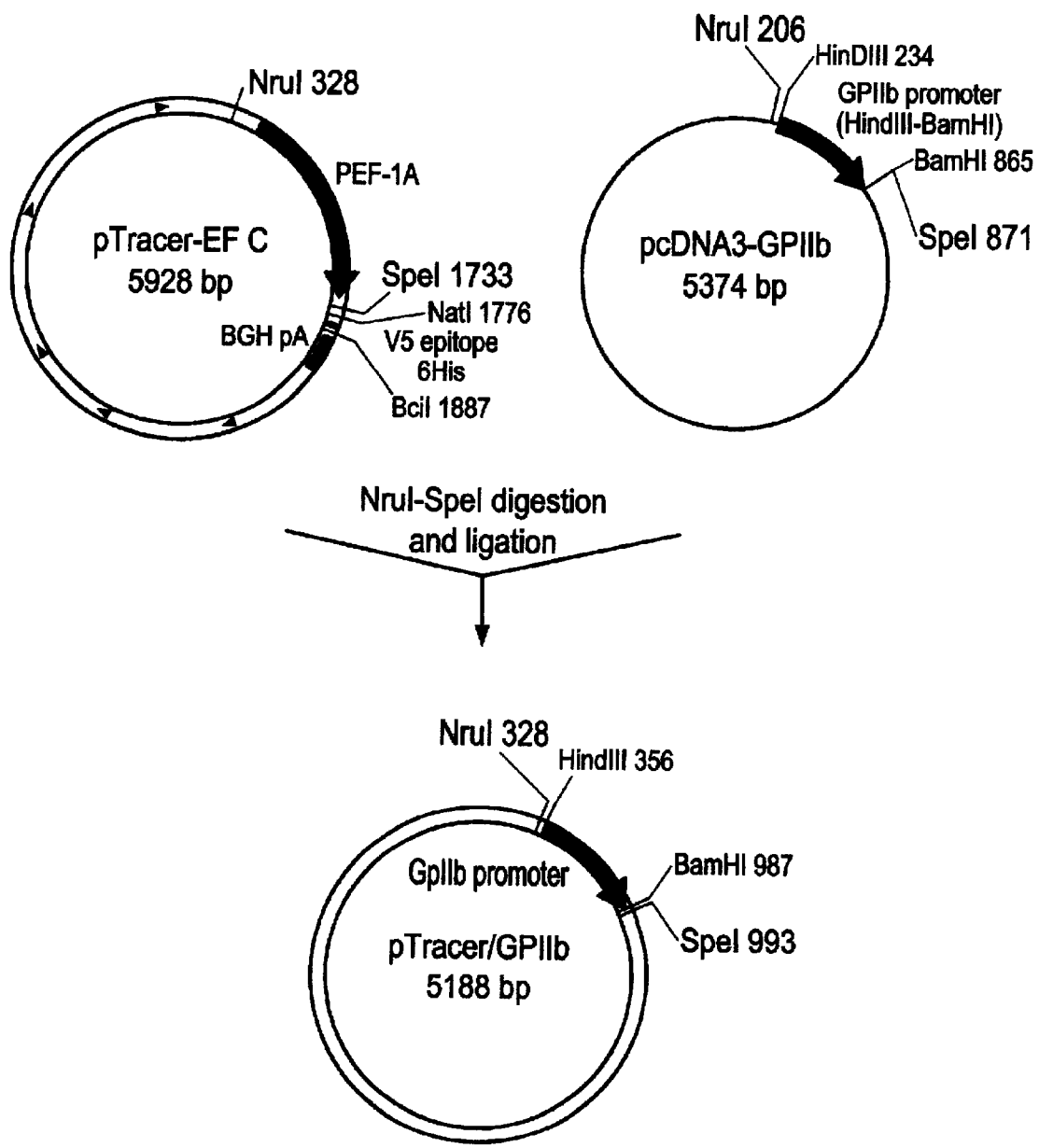
FIG. 2: Obtention of the pTracer/GPIIb Vector. pTracer-EF C and pcDNA3-GPIIb vectors were digested by NruI and SpeI. The opened pTracer and the NruI-SpeI GPIIb promoter were then ligated in order to obtain pTracer/GPIIb plasmid. Legendes: PEF-1α human elongation factor 1α promoter: 6His, Polyhistidine region; BGH pA, Polyadenylation region.
Figure 3:
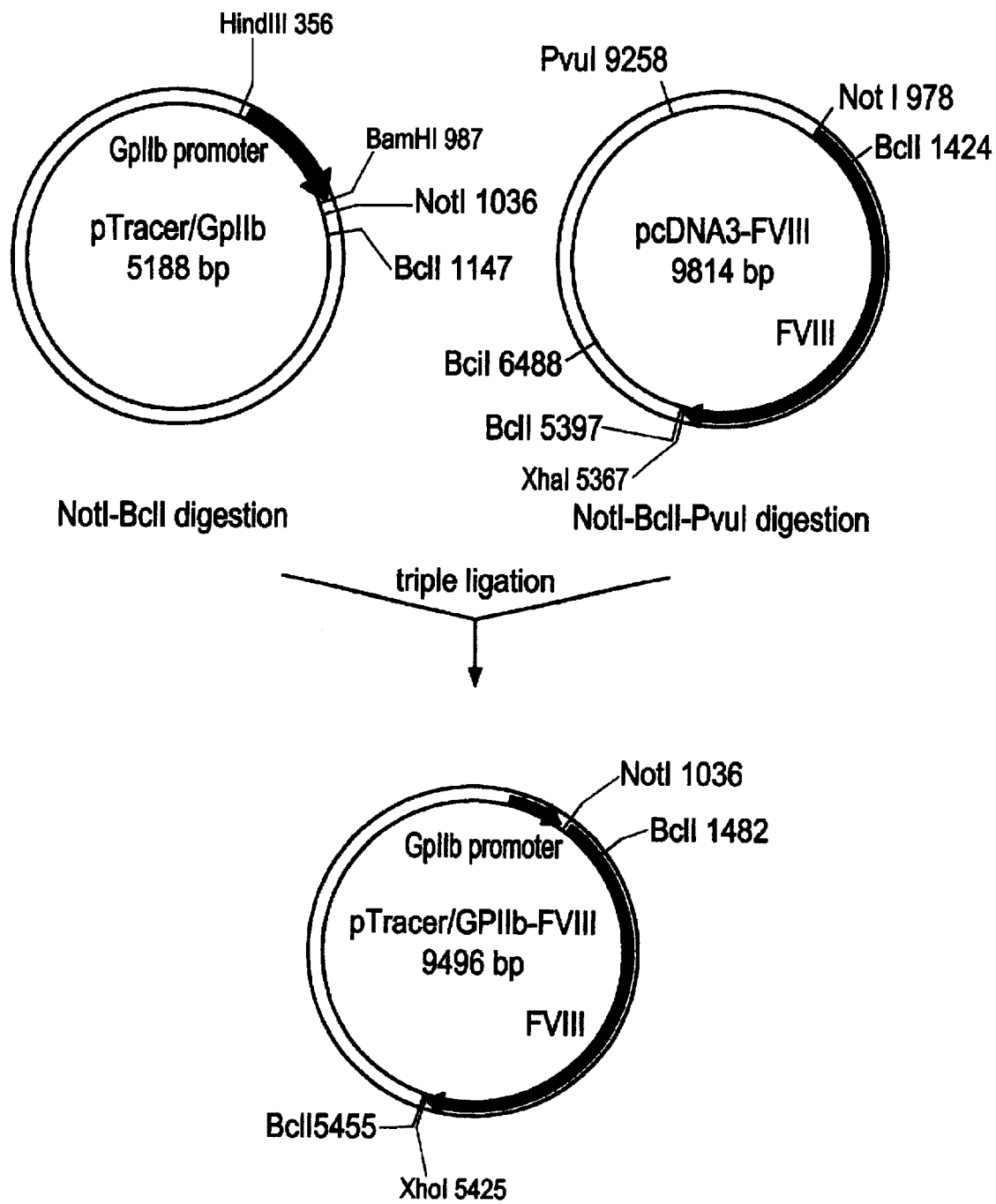
FIG. 3: Obention of the pTracer/GPIIb-FVIII Vector. pTracer/GPIIb vector was digested by NotI and BclI. FVIII cDNA was cloned between NotI and XhoI. PcDNA3-FVIII was digested by NotI, BclI and PvuI. The opened pTracer/GPIIb and the 2 FVIII fragments were ligated in order to obtain pTracer/GPIIb-FVIII plasmid.
Figure 4:
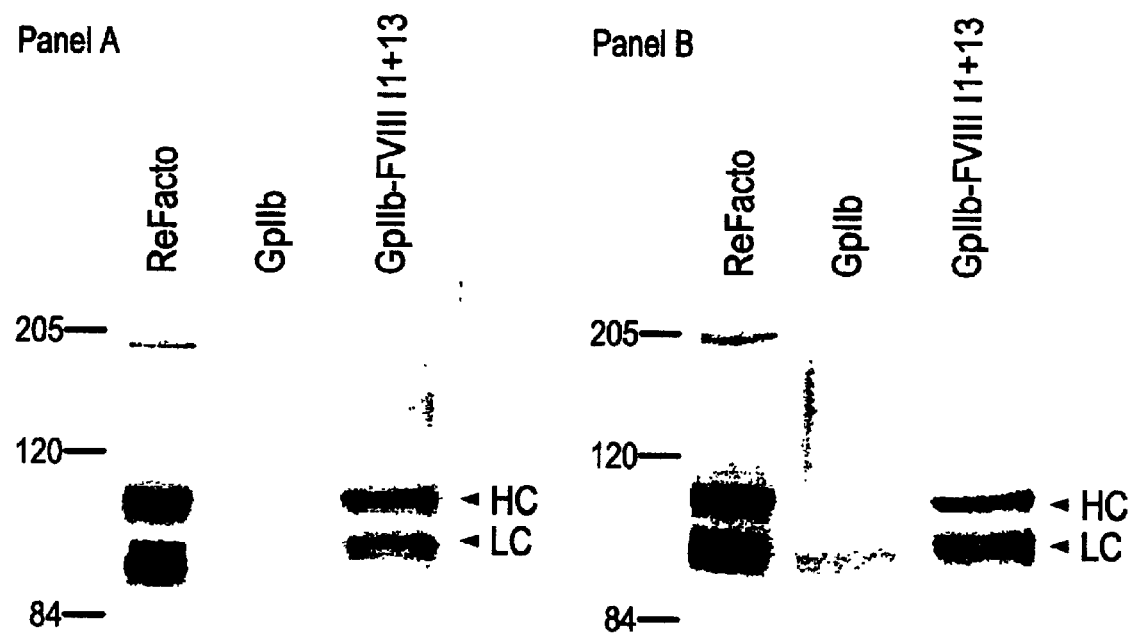
FIG. 4: Immunoblot Analysis of the Immunoprecipited FVIII Produced by the Transfected Dami Cells. PTracer/GPIIb- and GPIIb-FVIII I1+13 Dami cells were incubated with human vWF and PMA for 4 days. Supernantants were concentrated and thereafter subjected to vWF immunoprecipitation. Lysates were incubated with human vWF before immunoprecipitations. FVIII immunoblot analysis was realized using an anti-human FVIII antibody and detected the light chain (LC) and the heavy chain (HC). ReFacto® (5 ng) was used as control.

1. Andersson, L. O., Forsman, N., Huang, K., Larsen, K., Lundin, A., Pavlu, B., Sandberg, H., Sewerin, K., Smart, J.—Isolation and characterization of human factor VIII: molecular forms in commercial factor VIII concentrate, cryoprecipitate, and plasma. Proc Natl Acad Sci USA May 1986; 83(9):2979–83.
2. Ballen, K. K., Pitchie, A. J., Murphy, C., Handin, R. I., Ewenstein, B. M.—Expression and activation of protein kinase C isoforms in a human megakaryocytic cell line. Exp Hematol November 1996; 24(13:1501–8.
3. Gitschier, J., Wood, W. I., Garalka, T. M., Wion, K. L., Chen, E. Y., Eation D. H., Vehar, G. A., Capan, D. J., Lawn, R. M.—Characterization of the human factor VIII gene. Nature November 1984; 22–28; 312(5992):326.30.
4. Greenberg, S. M., Rosenthal, D. S., Greeley, T. A., Tantravahi, R., Handin, R. I. —Characterization of a new megakaryocytic cell line: the Dami cell. Blood December 1988; 72(6): 1968–77.
5. Hayward, C. P., Bainton, D. F., Smith, J. W., Horsewood, P., Stead, R. H., Podor, T. J., Warkentin, T. E., Kelton, J. G.—Multimerin is found in the alpha-granules of resting platelets and is synthesized by a megakaryocytic cell line. J Clin Invest June 1993; 91(6):2630–9.
6. Hill, S. A., Shaughnessy, S. G., Joshua, P., Ribau, J., Austin, R. C., Podor, T. J.—Differential mechanisms targeting type 1 plasminogen activator inhibitor and vitronectin into the storage granules of a human megakarykocytic cell line. Blood June 1996; 15:87(12):5061–73.
7. Laemmli, U. K. —Cleavage of structural proteins during the assembly of the head of bacteriophage T4. Nature August 1970 15:227(259):680–5.
8. Lang, M. W., Heffner, C. H., Williams, J. L., Peters, C., Prochawnik, E. V.—Regulation of megakaryocyte phenotype in human erythroleukemia cells. J Clin Invest April 1990; 85(4):1072–84.
9. Martin, P., Papayannopoulou, T.—HEL cells: a new human erythroleukemia cell line with spontaneous and induced globin expression. Science June 1982 11; 216 (4551):1233–5.
10. Tabilio. A., Rosa, J. P., Test, U., Kieffer, N., Nurden, A. T., Del Canizo, M. C., Bretan-Garius, J., Vainchenker, W.—Expression of platelet membrane glycoproteins and alpha-granule proteins by a human erytholeukemia cell line (HEL). EMBO J February 1984; 3(2):453–9.
11. Toole, J. J., Knopf, J. L., Wozney, J. M., Sultzman, L. A., Buecker, J. L., Pittman, D. D., Kaufman, R. J., Brown, E., Shoenaker, C., Orr, E. C. et al.—Molecular cloning of a cDNA encoding human antihaemophilic factor. Nature November 1984, 22–28; 312(5992):342–7.
12. Uzan, G., Prenant, M., Prandini, M. H., Martin, F., Marguerie, G.—Tissue-specific expression of the platelet GPIIb gene. J Biol. Chem May 1991 15; 226(14):8932–9.
13. Vehar, G. A., Keyt, B., Eaton, D., Rodriguez, H., O'Brien, D. P., Rotblat, F., Oppermann, H., Keck, R., Wood, W. I., Harkins, R. N. et al.—Structure of human factor VIII. Nature November 1984 22–28; 312(5992):337–42.
14. von der Vuurst, H., Hendriks, M., Lapetina, E. G., van Willigen, G., Akkerman, J. W.—Maturation of megakaryoblastic cells is accompanied by upregulation of G(s)alpha-L subtype and increased cAMP accumulation. Thromb Haemost May 1998; 79(5):1014–20.

What is claimed is:

1. A modified Factor VIII cDNA, comprising:
   a wild-type factor VIII cDNA,
   at least one intron, which has been inserted into at least one location of said wild-type factor VIII cDNA, wherein said at least one intron is not a factor VIII intron; and
   a promoter which targets the expression of said modified factor VIII cDNA to hematopoietic cells.

2. Modified Factor VIII cDNA as claimed in claim 1, wherein the B-domain of the wild-type factor VIII cDNA has been deleted.

3. Modified Factor VIII cDNA as claimed in claim 1, wherein said at least one intron is factor IX truncated intron 1.

4. Modified Factor VIII cDNA as claimed in claim 1, wherein said promoter is the human platelet glycoprotein IIb promoter.

5. Modified Factor VIII cDNA as claimed in claim 1, wherein said hematopoietic cells are megakaryocytes.

6. Modified Factor VIII cDNA as claimed in claim 1, wherein said at least one intron has been inserted into the wild-type factor VIII cDNA at the original positions of intron 1 and intron 13 of the genomic Factor VIII DNA.

7. A process for the production of Factor VIII, comprising:
culturing a cell line under conditions suitable to produce a polypeptide encoded by the modified Factor VIII cDNA as claimed in claim 1; and
recovering said polypeptide from the cell culture medium.

8. Process as claimed in claim 7, wherein the production of Factor VIII is stimulated by an inducer.

9. Process as claimed in claim 8, wherein said inducer is phorbol-12-myristate-13-acetate.

10. Process as claimed in claim 7, wherein said cell lint is human erythroleukemia (HEL) or Dami.

* * * * *